(12) United States Patent
Gayle

(10) Patent No.: US 7,987,720 B2
(45) Date of Patent: Aug. 2, 2011

(54) ULTRASONIC SENSING ARRAY SYSTEM AND METHOD

(76) Inventor: James Edward Gayle, Hermitage, TN (US)

( * ) Notice: Subject to any disclaimer, the term of this patent is extended or adjusted under 35 U.S.C. 154(b) by 0 days.

(21) Appl. No.: 12/176,688

(22) Filed: Jul. 21, 2008

(65) Prior Publication Data

US 2009/0013764 A1  Jan. 15, 2009

Related U.S. Application Data

(63) Continuation of application No. 12/132,835, filed on Jun. 4, 2008, now abandoned, which is a continuation of application No. 11/055,222, filed on Feb. 10, 2005, now Pat. No. 7,387,026, which is a continuation-in-part of application No. 10/320,671, filed on Dec. 17, 2002, now abandoned.

(60) Provisional application No. 60/341,553, filed on Dec. 17, 2001.

(51) Int. Cl.
*G01N 29/02* (2006.01)

(52) U.S. Cl. ...................... 73/592; 73/40.5 A

(58) Field of Classification Search ............... 73/40.5 A, 73/632, 592; 340/426.16, 425.5, 605
See application file for complete search history.

(56) References Cited

U.S. PATENT DOCUMENTS

| | | | |
|---|---|---|---|
| 4,719,801 A * | 1/1988 | Blaser et al. | 73/592 |
| 4,901,576 A * | 2/1990 | Rademacher | 73/592 |
| 6,430,988 B1 * | 8/2002 | Watanabe | 73/40.5 A |

* cited by examiner

*Primary Examiner* — Hezron Williams
*Assistant Examiner* — Tamiko D Bellamy
(74) *Attorney, Agent, or Firm* — Wayne Edward Ramage; Baker Donelson

(57) ABSTRACT

A system and method for detecting leaks in substantially closed objects, such as automobiles, airplanes, tanks, and other vehicles, using an ultrasonic transmitter and one or more ultrasonic sensors or receivers supported on a frame. Ultrasonic amplitude readings obtained from the sensor or sensors are processed to determine if they are representative of a defective or leaking object. The position of the leak may be determined by examining the readings from individual sensors. The system is particularly well-adapted for use in detecting defects and leaks in automobiles on an assembly line without interrupting the assembly process or damaging the automobile.

17 Claims, 3 Drawing Sheets

ULTRASONIC SENSING ARRAY SYSTEM AND METHOD

This application is a continuation of U.S. patent application Ser. No. 12/132,835, entitled "Ultrasonic Sensing Array System and Method," filed Jun. 4, 2008 by James Edward Gayle, now abandoned, which is a continuation of U.S. patent application Ser. No. 11/055,222, entitled "Peripheral Ultrasonic Sensing Array System and Method," filed Feb. 10, 2005 by James Edward Gayle, now U.S. Pat. No. 7,387,026, which is a continuation-in-part of U.S. patent application Ser. No. 10/320,671, entitled "Ultraphonics Array System," filed Dec. 17, 2002 by James Edward Gayle, now abandoned which claims the benefit of and priority to U.S. Provisional Patent Application No. 60/341,553, filed Dec. 17, 2001 by James Edward Gayle, and is entitled to those filing dates for priority.

The specifications, drawings, attachments, and disclosures of U.S. Provisional Patent Application No. 60/341,553, U.S. patent application Ser. No. 10/320,671, U.S. patent application Ser. No. 11/055,222, and U.S. patent application Ser. No. 12/132,835 are incorporated herein in their entireties by reference.

FIELD OF THE INVENTION

The present invention is directed toward the field of ultrasonic monitoring and detection systems. More particularly, the present invention is directed toward an ultrasonic monitoring system for detecting defects or leaks in manufactured items.

BACKGROUND OF THE INVENTION

The present invention is the result of extensive, long-term research by the present inventor into leak detection methods and devices that are prevalent throughout manufacturing industries today. Unfortunately, many of the evaluation and detection methods and processes in use today are destructive, time consuming, messy, unreliable, expensive, unsafe and fail to provide accurate results. For example, water spray booths used for leak detection in the automotive industry ruin millions of dollars of vehicle accessories per year. In addition, soap bubble testing for leaks in air, liquid, or gaseous systems are inaccurate and create messes that can contribute to unsafe, slip and fall type potential hazards. Ultrasonic leak monitoring is also used in the automotive industry to detect vehicle defects and leaks. However, the hand held ultrasonic sensing devices typically used are time consuming to use and produce inconsistent results that are difficult to compare over time. Thus, the present inventor's research revealed that a method of leak detection that was more cost efficient and consistent and created a cleaner, safer manufacturing environment would be well received by the manufacturing community.

In response to the above described shortcomings, Jimmy Gayle developed the new and improved "Peripheral Ultrasonic Sensing Array System and Method" as described herein.

BRIEF SUMMARY OF THE INVENTION

The present invention was created to utilize recent technological advances to help progressive companies enhance their quality monitoring systems and achieve more reliable and dependable results in the quality of their products and their manufacturing processes. This diagnostic and detection system also improves the environment through the conservation of energy and resources and the creation of a more employee friendly atmosphere. Great cost efficiencies are also realized through reduced detection time and the increased ability to precisely locate leaks.

Accordingly, an embodiment of the present invention is directed toward a system for detecting a liquid or gas leak in a substantially enclosed object. The system includes an ultrasonic transmitter positioned in the enclosed object that produces and transmits ultrasonic frequency sound waves. A frame is included that has a plurality of ultrasonic sensors positioned around the internal perimeter of the frame for detecting the ultrasonic frequency sound waves. The frame is constructed to minimize ultrasonic reflections. The internal perimeter of the frame corresponds to an outline of the substantially enclosed object. At least one object position sensor positioned on the frame senses a position of the object with respect to the frame. A conveyor moves the object through the frame at a predetermined speed. A receiver receives ultrasonic frequency signals from the sensors and converts the ultrasonic frequencies signals to lower frequency signals. An analog-to-digital converter converts the lower frequency signals to digital data. Most preferably, a Hartley oscillator is used to convert the ultrasonic frequency signals to a lower frequency. A computer terminal coupled to the digital to analog converter receives, analyzes and stores the digital data to determine the size and location of any leaks in the object being tested. More particularly, the computer terminal compares an amplitude of the ultrasonic frequency signals to a predetermined alarm threshold to determine if an unacceptable leak is present.

Another embodiment of the present invention is directed toward a method of locating leaks in a substantially enclosed object. In accordance with the method, an ultrasonic transmitter is placed inside of the substantially enclosed object that produces ultrasonic sound waves at a predetermined frequency. The frequency of the transmitter is altered if interference is present at the predetermined frequency. The object is moved through a peripheral ultrasonic sensing array at a predetermined speed. The peripheral ultrasonic sensing array is mounted on a frame that is constructed to minimize ultrasonic reflections and signal interference. A series of ultrasonic sensor readings is obtained from the ultrasonic sensing array as the object moves through the peripheral ultrasonic sensing array. The ultrasonic frequency signals from the peripheral ultrasonic sensing array are converted to signals having a lower frequency. The lower frequency signals are then converted into digital data. The amplitude of the ultrasonic sensor readings is compared to a threshold amplitude level to determine if the threshold amplitude level has been exceeded. An image of the object is displayed that contains a visual indication of the amplitude and of at least some of the ultrasonic sensor readings and the location on the object from which the readings were obtained.

DETAILED DESCRIPTION OF THE INVENTION

The knowledge and experience of Jimmy Gayle in the area of ultrasonic detection was put to use in the invention of a new ultrasonic sensing product which solves the above described problems by providing a cost effective, easy to use, ultrasonic detection system that is readily adaptable to a modern manufacturing environment. More particularly, it was discovered that by utilizing amplitude sensitive ultrasonic sensing technology and selecting the proper frequency level and modulation method for sending and receiving the ultrasonic signals, an extremely reliable and accurate ultrasonic leak detection device could be created.

Figure 1:
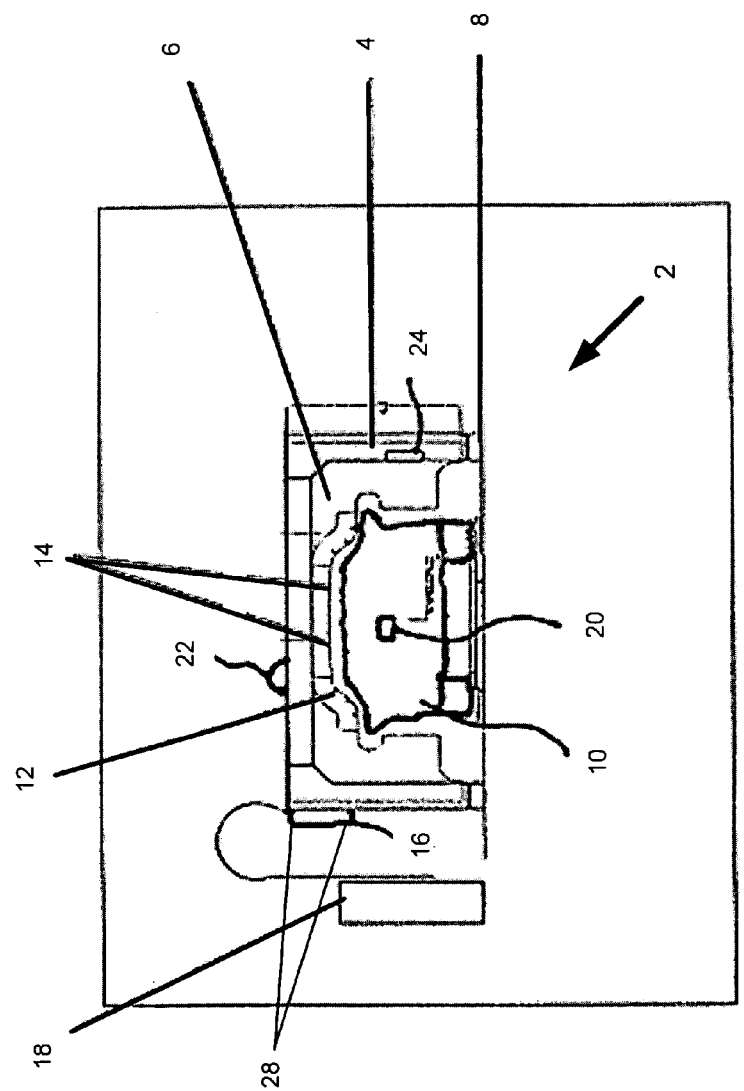
FIG. 1 is an illustration of an ultrasonic sensing system for use in the automotive industry in accordance with an embodiment of the present invention.

Referring now to FIG. 1, a diagram of an embodiment of the present invention is shown. The system 2 consists of a substantially rectangular frame 4 having an insertable, customized sensing silhouette 6 or template 6. The frame 4 is positioned over a section of a manufacturing line 8 so that the products being manufactured on the line 8 pass beneath the frame 4. The frame 4 is preferably at least approximately three feet in depth to help shield the silhouette 6 from any ambient ultrasonic noise in the environment. The silhouette 6 is shaped to conform to the outer dimensions of the particular product whose quality is being monitored. For example, with regard to the embodiment of FIG. 1, the product is a sports car 10. However, the present invention is equally well adapted for applications involving any substantially enclosed object such as pipes, tubes, airplanes, tanks, etc. Thus, the interior silhouette 6 of the framed 4 is shaped to conform to the outer dimensions of the sports car. The silhouette 6 is adapted to be easily removed from the frame 4 and replaced with a different silhouette such that different silhouettes 6 could be used to adapt the process for use with different makes and models of automobiles without requiring a substantial disruption to the manufacturing process. A plurality of ultrasonic sensors 12 are positioned along the inner periphery of the silhouette 6. In a preferred embodiment, there are 16-32 ultrasonic sensors placed around the internal periphery of the silhouette 6 including the floor. However, it will be appreciated that the number of sensors 12 used can be varied depending upon the object being evaluated. The ultrasonic sensors 12 are used to detect ultrasonic sound waves being produced by an ultrasonic transmitter 20 that has been positioned in the automobile or vessel being tested.

The basic idea is that any ultrasonic sound waves detected outside of the vehicle having an amplitude above a certain threshold level are most likely due to a leak or manufacturing defect in the automobile 10. To test an automobile 10, the ultrasonic transmitter 20 is placed inside of an automobile that is ready for its final evaluation. If multiple inspection lines 8 are running next to each other, different frequency signals may be used on each line to prevent cross contamination. The transmitter 20 is placed in approximately the same location such that each vehicle 10 is tested under approximately the same conditions. The ultrasonic transmitter preferably produces approximately 40 kHz frequency ultrasonic sound waves. The 40 kHz frequency is selected because the wavelengths are short enough to penetrate through minute and winding open passage ways and yet long enough not to attenuate too rapidly or penetrate solid surfaces. This allows the system 2 to detect both water leaks and wind noise pathways. In a most preferred embodiment, the transmit frequency is selected from a range of approximate 38 kHz to approximately 42 kHz based upon the frequency response of the vessel being tested to the transmitted frequency. In such an embodiment, the transmitter is placed in the vessel and the frequency of the transmitted signal is calibrated to insure the proper frequency response is obtained. The frequency that penetrates the vessel with the highest amplitude is then selected as the transmit frequency.

Unfortunately, sound waves in the 40 kHz frequency range are inaudible and may interfere with computer equipment. Therefore, as discussed in more detail below, the received signals are preferably reflected by a Hartley oscillator 28 to down convert them to a frequency of less than approximately 4000 hertz. Although the use of a Hartley oscillator 28 is preferred, it will be appreciated by those skilled in the art that a variety of other methods such as heterodyning could be used to down convert the frequency of the signals. This down conversion in frequency of the signals received by the receivers 16 improves the ability to manage the signals without aliasing and to observe variations in the signals without significantly affecting the accuracy of the process. Down converting the signals further decreases the required sampling rate for the analog to digital converters that sample the signals.

As the automobile 10 is drawn through the silhouette 6 at a substantially constant rate of speed, an ultrasonic sensor 12 reading is obtained from each sensor 12 at a predetermined time interval. Optical sensors 14 are also positioned in the silhouette to determine precisely when the automobile 10 enters and exits the frame 4. Most preferably, at least two optical sensors 14 are positioned along the silhouette 6 to detect different areas of the automobile 10 as it enters and exits the frame such that false alarms due to abnormal or unexpected objects passing through the frame 4 are minimized. By correlating the position of the vehicle 10 obtained from the optical sensors 14 with the time at which the ultrasonic sensor 10 readings are taken, the vehicle 10 is essentially divided into a series of slices wherein a set of ultrasonic amplitude readings are obtained around the periphery of the vehicle 10 for each slice.

As will be apparent to those skilled in the art in light of the present disclosure, the number of sensors 12 positioned on the object template 6 varies depending on the size of the object being monitored and/or the degree of evaluation that is needed for a particular vehicle or other manufactured object. The arch 4 or template 6 can also be adjusted with regard to height and width dimensions to accommodate the testing of larger or smaller objects. The transducers 12 can be moved in and out on a horizontal basis or on a vertical basis to accommodate particular out riggings or structures that are present on the tested object. However, in a most preferred embodiment, the template 6 is shaped to correspond to an outline or silhouette of the object being evaluated. This allows the sensors 12 to be located closer to the source of any leak and, thus, improves the accuracy with which the leak can be located.

The ultrasonic sensors 12 are electrically connected to a set of receivers 16 mounted on the frame 4 which are in turn in communication with a remote computer terminal 18 that controls and monitors the entire process. As discussed above, the receivers 16 include frequency converters which convert the received ultrasonic frequency sensor signals into a lower frequency signal and analog-to-digital converters that convert the reduced frequency signal to digital data. Down converting the frequency of the received signal allows slower speed, and thus less expensive, analog-to-digital converters to be used. In addition, the lower frequency signals are less likely to interfere with the ultrasonic sensors 12 or computer electronics.

The receivers 16 are connected to a system monitoring computer 18 that records and analyzes the digital data received from the receivers. As the vehicle 10 moves through the frame 4, the position sensors 14, which are preferably optical sensors 14, detect the presence and position of the vehicle 10. Once the vehicle's 10 entry into the frame 4 has been detected, the computer 18 begins recording and storing sensor 12 readings at predetermined intervals. These intervals may be time based, i.e. every 1/10$^{th}$ of a second, or distance based, i.e. after the vehicle 10 has been carried four inches forward by the assembly line 8. If desired, a position encoder may be coupled to the assembly line 8 to provide distance based triggering for the taking of the slices. Thus, the sensor 12 readings are obtained from virtual slices of the vehicle 10 as it passes through the arch 4. Most preferably, each vehicle 10 is divided into 40-60 slices. However, the larger the number of slices, the more precisely the location of any leaks can be determined. Conversely, taking a smaller number of slices from a particular location on the vehicle reduces the data requirements of the system 2 and may improve the cost efficiency of the system 2. The system computer 18 has a display that displays a graphical representation of the process in real time as it proceeds. Most preferably, the system computer 18 displays an image of the object being evaluated along with a received signal strength indication for each sensor 12 displayed at each location along the object image where a sensor reading was obtained.

The sensors 12 detect ultrasonic sound produced by the transmitter 20 that has been placed in the vehicle 10. The amplitude of the ultrasonic sound detected by each ultrasonic sensor 12 depends upon a number of factors such as the size of the leak in the automobile 10, the distance of the sensor 12 from the ultrasonic transmitter 20 producing the ultrasonic sound, the amplitude of the ultrasonic signal produced by the transmitter 20, the amplitude of any ultrasonic reflections or ambient noise, damping brought about by the proper use of angled construction techniques and sound dampening surfaces and a variety of other factors. Therefore, in order to extract useful information concerning the size of any leak from the amplitude of the sensors 12 output, it is necessary to reduce variations in the received ultrasonic amplitude due to variations in the distance from the ultrasonic transmitter 20 to the ultrasonic sensors 12, variations in the amplitude of the ultrasonic sound produced by the transmitter 20, ambient ultrasonic sound and ultrasonic reflections and any other factors unrelated to the leak size. As discussed in more detail herein, the present invention uses a variety of techniques to insure a minimum amount of variability in these factors.

The computer monitoring system 18 receives digital data from the receivers 16. The conversion of the analog sensor 12 signals into digital data is beneficial in a number of respects. For example, the digital conversion allows the sensor 12 signals to be digitally stored such that they can be processed and referenced over an extended period of time. In addition, by positioning the analog-to-digital converters in the receivers 16 as close as possible to the sensors 12, any degradation of the analog sensor 12 signals due to their propagation along the connecting wires can be minimized. Also, as discussed in more detail below, the conversion to digital data facilitates long term data storage and analysis.

Software in the monitoring system evaluates the sensors 12 output at the predetermined frequency and provides the user with much more accurate and distinctive information than has previously been available due to the inherent presence of excessive background noise, which often produces false readings. One of the ways in which the software accomplishes this is by zeroing out any ambient ultrasonic noise. This is accomplished by measuring the amplitude of ultrasonic noise received by the sensors 12 when the transmitter 20 is not transmitting and then digitally subtracting this noise from subsequent test readings. The software also provides a much improved method of recording and retaining data and, thus, vastly increases the analytical potential of the monitoring system. Since the acoustical information and/or sound energy is converted to a digital state that can be easily evaluated and stored, the amplitude readings that the sensors 12 receive and send to the computer 18 can be more closely examined and compared with prior readings for greater analytical accuracy. The digital data analysis also greatly enhances the ability to determine the size and volume of the leak through its amplitude without the need to extensively filter out background noises. The diagnostic process also vastly improves the reliability of the output information by using a defined amplitude signal having a frequency in the range of 40 kHz which can be easily isolated form any background noise.

As discussed above, to prevent variations in signal amplitude due to variations in distance, the ultrasonic sensors 12 are positioned along the silhouette 6 such that each sensor 12 is approximately the same distance from the vehicle as the other sensors 12. Since the attenuation of the transmitted ultrasonic sound is fairly constant for a given distance, the amplitude of the ultrasonic signals received by each of the sensors 12 will be attenuated in an approximately equal amount due to the form fitting silhouette 6. In addition, since the sensors 12 position and configuration remains constant as a large number of objects pass through the arch 4, the amplitude of the sensor readings obtained from one object can be meaningfully compared to the sensor readings from another object. Conversely, prior art ultrasonic sensors are placed at varying and often unknown distances from the object being tested. Therefore, the absolute amplitude of the received ultrasonic signals in prior art devices is determined in part by the sensor's unknown and varying configuration and distance away from the transmitting source, not the size of the leak. Thus, the amplitude information in prior art devices is essentially useless for determining the size of a leak. In addition, since the amplitude of the received signal is varying uncontrollably in these prior art devices, amplitude information from one test can not be accurately compared to amplitude information from another test. Prior art sensing systems typically rely upon contemporaneous amplitude shifts from a single sensor that are audibly monitored to determine individual leak locations. Thus, the use of an equidistant template 6 and a standardized system configuration as set forth in the present invention helps preserve any leak information contained in the amplitude of the received ultrasonic signal and represents a substantial improvement upon the prior art.

As discussed above, the template 6 has a number of features that make it particularly well suited to its ultrasonic sensing functionality. For example, the template 6 preferably includes an internal profile that customized for and corresponds to a particular make and model of vehicle. This insures that the sensors 10 are a predetermined distance from the surface of the vehicle 10 as it passes through the frame. In addition, users of the system 2 can order a new silhouette 6 for a new vehicle production line and then simply install the delivered silhouette 6 by connecting the sensor 12 wires from the silhouette 6 to the receivers 16. The template 6 is also preferably constructed from a relatively easily breakable material such as a Styrofoam sheet that will not damage any vehicle 10 or individual that accidentally comes into contact with the insert 6. This is particularly beneficial in manufacturing environments where safety is paramount. The use of metal in the frame 4 and template 6 is also avoided since the metal may interfere with the transmission of the ultrasonic signals along the wires running from the sensors 12 to the computer terminal 18. In addition, the interior surfaces of the frame 4 are preferably covered with a sound absorbing material that absorbs ultrasonic waves and prevents reflections of ultrasonic waves from contaminating the test results. Right angle corners on the frame 4 are also preferably smoothed out to prevent harmful ultrasonic reflections from contaminating the test results.

The present invention was developed with the intent of being easy to use with little or no interruption in the flow of manufacturing operations and to be non-intrusive to the object being tested, and to those conducting the testing, while simultaneously producing very reliable results. As the automobile 10 moves through the frame 4, each ultrasonic sensor 12 detects the absolute amplitude of ultrasonic waves being radiated by the ultrasonic transmitter 8 placed within the automobile 10. If an imperfection exists in the structure of the vehicle 10 such as a hole or a gasket that is not seated properly or a windshield that is not water tight, the sensor 12 for that designated area will pick up a relatively high amplitude ultrasonic signal emitted through the opening as the automobile 10 moves past the sensor 12. The higher frequency/smaller wavelength of the ultrasonic sound can pass through very minute openings making the detection of extremely small leaks possible. Furthermore, since all of the sensors 12 are approximately the same distance from the exterior of the vehicle, a higher amplitude signal will correspond to a larger leak. Inconsistency in measurement parameters has not allowed prior art devices to accurately compare amplitude readings taken at different times from different locations such that they can be trended and analyzed in this manner.

If an ultrasonic reading exceeding the predetermined threshold is detected, the computer program residing in the remote terminal 18 pinpoints the sensor 12 involved and records the location of the imperfection while the vehicle 10 passes through the arch-like frame 4 on its predetermined track. The accuracy of the location is determined by the number of readings/slices taken and the number of sensors 12 present. If the detected amplitude is at or above a predetermined threshold alarm level that has been selected by the engineers as indicative of a rejectable defect with respect to the particular automobile 10, it will cause an alarm, such as a light 22 on the top of the array, to flash thereby signaling that the automobile 10 is being rejected for potential leakage areas. The computer 18 will then provide the exact location of the leak so that the appropriate repairs may be performed. The location is preferably determined by the relative strength of the signal sensed by each ultrasonic sensor 10. The operator of this system will preferably also have a hand-held receiver that is tuned in to the frequency of the transmitter 20 to allow him to evaluate rejected vehicles off line, implement the needed repairs to the vehicle 10, and re-check the vehicle 10 to insure that it meets specifications.

As the vehicle 10 passes through the frame 4, a bar code reader 24 reads a bar code on the vehicle that identifies exactly which particular automobile 10 is being evaluated. While a bar code system is preferred, those skilled in the art will appreciate that alternative identification systems may be used. The identification means attached to the vehicle 10 is associated with the vehicle's identification number (VIN). The system reads the bar code and tracks the identified vehicle 10 as it proceeds through the array during this leak detection test. This allows the process to be individually tailored to a particular automobile. In general, the computer 18 processes a given vehicle 10, collects data that determines whether it passes or fails the test, and defines where the problem is located and what the problem is. This data is then combined with other similar data for the purpose of analyzing, trending and making improvements in the manufacturing process over time. This data can also be used to determine those areas of the manufacturing process that are performing well and those that are not. For example, repeatedly detecting leaks along a door seal may indicate that there is a problem with the component or assembly process.

These evaluations, data, and percentages are powerful decision-making tools that serve as a foundation upon which to improve the manufacturing processes. For example, the system possesses the ability to be combined with other manufacturing process information and data within that location as well as with multiple plant locations or even company wide. Furthermore, because the receivers 16 on the arch 4 process the signals immediately and convert them to a lesser frequency, the signals can be dealt with at a more rapid rate and stored in a smaller memory than in typical systems. Thus, embodiments of the present invention create the opportunity for the testing process to be operated at a pace 10 times faster than that which most typical assembly lines can achieve.

The software running on the computer 18 has the ability to produce a wave form based on the sensor data from the automobile and, also, to run real time Fast Fourier Transforms so that the exact frequency that is being transmitted from within the vehicle can be determined and a user can verify that the system 2 is receiving the same frequency. Due to the construction of the frame 4, very little interference occurs and no phantom sounds are transmitted which could produce false readings. Thus, system verification can be utilized to provide the operator confidence that the system is producing factual information.

Figure 2:
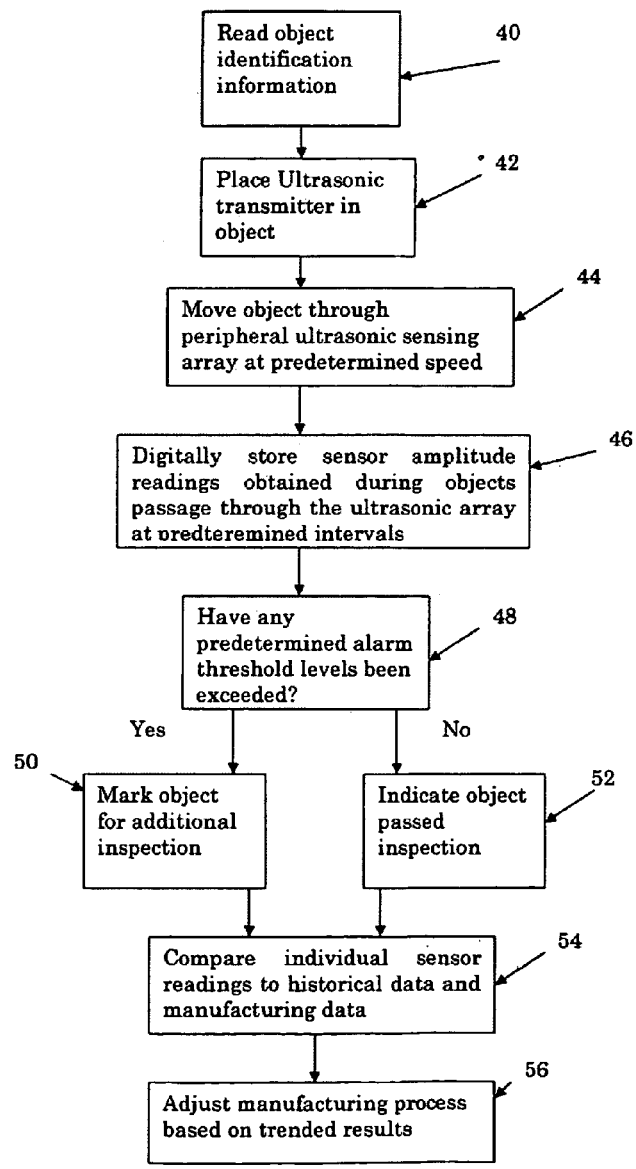
FIG. 2 is a flow chart of a method of detecting a leak in accordance with an embodiment.
Figure 3:
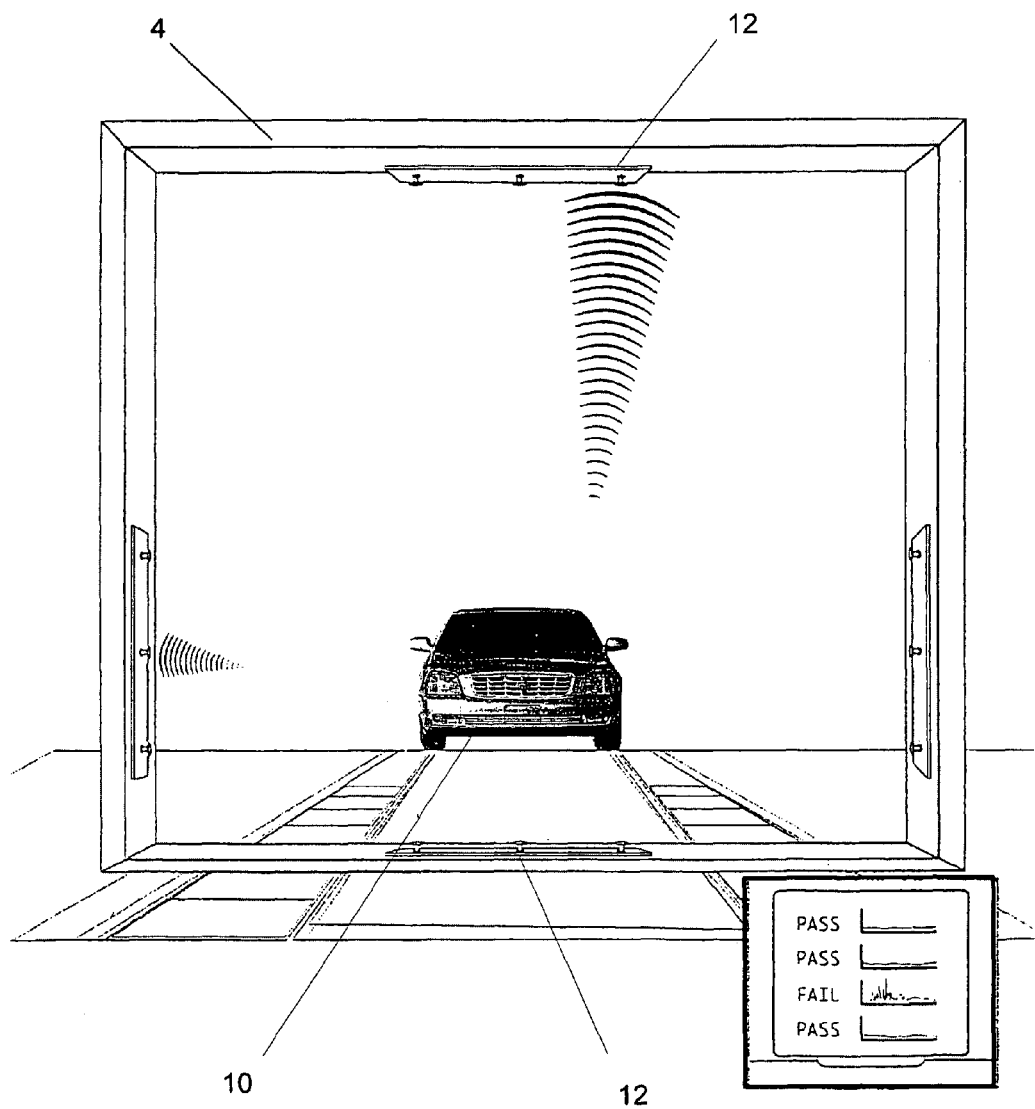
FIG. 3 is an illustration of an ultrasonic sensing system in accordance with another embodiment of the present invention.

Referring now to FIG. 2, a flow chart of a preferred method of using the system of FIG. 1 is set forth. The method begins in step 40 with the reading of identification information from the object to be tested. As discussed above, this identification information allows any detected defects to be associated with particular objects. Next, in step 42, an ultrasonic transmitter is placed in the object. In step 44, the object is moved through a peripheral ultrasonic sensing array as described above at a substantially constant speed. As the object proceeds through the peripheral sensing array, sensor readings are obtained at predetermined intervals and digitally stored as shown in step 46. The obtained sensor readings are then compared to predetermined alarm threshold levels in step 48 to determine if any alarm thresholds have been exceeded. If an alarm threshold has been exceeded, an alarm is produced and the object is marked for further evaluation as set forth in step 50. If no alarm thresholds are exceeded, an indication that the object passed the test is produced in step 52. The method then proceeds to step 54 wherein the individual sensor reading are compared to historical and manufacturing data. Finally, in step 56 the manufacturing process for the objects is adjusted based upon trended results of the monitoring process.

Thus, although there have been described particular embodiments of the present invention of a new and useful Peripheral Ultrasonic Sensing Array System and Method, it is not intended that such references be construed as limitations upon the scope of this invention except as set forth in the following claims.

I claim:

1. A system for detecting a liquid or gas leak in a substantially enclosed object, said system comprising:
   an ultrasonic transmitter positioned in said enclosed object for producing ultrasonic frequency sound waves;
   a plurality of ultrasonic sensors positioned to form a silhouette about said enclosed object for detecting said ultrasonic frequency sound waves and producing ultrasonic frequency signals;
   an analog-to-digital converter for converting said ultrasonic frequency signals to digital data; and
   a computing device coupled to said analog-to-digital converter for receiving, analyzing and storing said digital data, further wherein said computing device compares at least one amplitude of said ultrasonic sensor data to a threshold amplitude level to determine if said threshold amplitude level has been exceeded and determining if a leak is present in said object based upon said comparison.

2. The system of claim 1, further comprising a receiver for receiving the ultrasonic frequency signals from said sensor or sensors and converting said ultrasonic frequencies signals to lower frequency signals which are in turn provided to said analog-to-digital converter.

3. The system of claim 1, wherein said computer device compares a strength of a received ultrasonic frequency signal to a predetermined alarm threshold and produces an alarm if said threshold is exceeded.

4. The system of claim 1, wherein said sensor or sensors are in proximity to said substantially enclosed object.

5. The system of claim 1, further comprising at least one object position sensor for sensing a position of said object with respect to said plurality of sensors.

6. The system of claim 1, wherein said computing device determines a location of a potential leak based upon a detected amplitude of said ultrasonic frequency sound waves.

7. The system of a claim 1, wherein said receiver further comprises a Hartley oscillator for converting the ultrasonic frequency signals to a lower frequency.

8. The system of claim 1, wherein the object and the plurality of sensors are moved relative to each other.

9. A method of locating leaks in a substantially enclosed object, said method comprising:
placing an ultrasonic transmitter inside of said substantially enclosed object wherein said ultrasonic transmitter produces ultrasonic sound waves at a predetermined frequency;
moving said object at a predetermined speed through a plurality of ultrasonic sensors positioned to form a silhouette about said enclosed object;
comparing at least one amplitude of said ultrasonic sensor readings to a threshold amplitude level to determine if said threshold amplitude level has been exceeded and determining if a leak is present in said object based upon said comparison.

10. The method of claim 9, further comprising converting ultrasonic frequency signals from said peripheral ultrasonic sensing array to signals having a lower frequency.

11. The method of claim 10, further comprising converting said lower frequency signals into digital data.

12. The method of claim 9, further comprising altering a frequency of said transmitter based upon a physical structure of said object or the presence of interference at said predetermined frequency.

13. The method of claim 9, further comprising the step of displaying an image of said object wherein said displayed image contains a visual indication of the amplitude of at least some of said ultrasonic sensor readings and a location on said object from which they were obtained.

14. The system of claim 1, wherein the object is a motor vehicle.

15. The system of claim 1, wherein the object is an airplane.

16. The method of claim 9, wherein the object is a motor vehicle.

17. The method of claim 9, wherein the object is an airplane.

* * * * *